US012667245B1

(12) United States Patent
Taefi et al.

(10) Patent No.: US 12,667,245 B1
(45) Date of Patent: Jun. 30, 2026

(54) MOTORIZED ENDOSCOPIC INSTRUMENT DRIVE MODULE

(71) Applicants: Amir Taefi, Sacramento, CA (US); Albert K Chin, Palo Alto, CA (US)

(72) Inventors: Amir Taefi, Sacramento, CA (US); Albert K Chin, Palo Alto, CA (US)

( * ) Notice: Subject to any disclaimer, the term of this patent is extended or adjusted under 35 U.S.C. 154(b) by 0 days.

(21) Appl. No.: 19/173,768

(22) Filed: Apr. 8, 2025

(51) Int. Cl.
*A61B 1/00* (2006.01)

(52) U.S. Cl.
CPC ...... *A61B 1/00133* (2013.01); *A61B 1/00128* (2013.01)

(58) Field of Classification Search
CPC ............ A61B 1/00133; A61B 1/00128; A61B 1/00066; A61B 1/0016
See application file for complete search history.

(56) References Cited

U.S. PATENT DOCUMENTS

| | | | | |
|---|---|---|---|---|
| 5,236,423 | A * | 8/1993 | Mix ................... | A61M 25/0111 600/920 |
| 6,872,178 | B2 * | 3/2005 | Weinberg ................ | A61B 1/31 600/114 |
| 8,419,623 | B2 | 4/2013 | Garcia et al. | |
| 8,512,227 | B2 | 8/2013 | Murakami et al. | |
| 9,649,096 | B2 | 5/2017 | Sholev et al. | |
| 10,835,108 | B2 | 11/2020 | Sholev et al. | |

| | | | | |
|---|---|---|---|---|
| 2005/0267327 | A1 | 12/2005 | Iizuka et al. | |
| 2011/0319708 | A1 * | 12/2011 | Shapiro .............. | A61B 1/00133 600/104 |
| 2015/0112134 | A1 * | 4/2015 | Suehara ............... | A61B 1/0052 600/109 |
| 2015/0342445 | A1 * | 12/2015 | Jones ................. | A61B 1/00133 600/106 |
| 2019/0142247 | A1 * | 5/2019 | Maeda ................... | A61B 1/018 600/106 |
| 2020/0329950 | A1 * | 10/2020 | Shear ................... | A61B 1/0016 |
| 2022/0125282 | A1 | 4/2022 | Abitbol | |
| 2022/0273166 | A1 * | 9/2022 | Nord .................. | A61B 1/00133 |
| 2023/0018532 | A1 | 1/2023 | Serra-Torrent et al. | |

FOREIGN PATENT DOCUMENTS

| | | |
|---|---|---|
| DE | 202012011472 U1 | 4/2014 |
| JP | 1986037938 B2 | 1/1981 |
| JP | 1982117823 A | 7/1982 |

* cited by examiner

*Primary Examiner* — Anh T Nguyen
*Assistant Examiner* — Rynae E Boler
(74) *Attorney, Agent, or Firm* — Craig Litherland

(57) ABSTRACT

A module for feeding and withdrawing an endoscopy operating instrument into/from an endoscope to prevent injury to tissue. The module includes an interface for removably attaching to an endoscope. The module includes a motor that drives a pair of wheels to advance the instrument into the endoscope. The wheels may be constrained on their sides to prevent binding when gripping the instrument. The motor may be turned on by a user operated button or a sensor that detects the instrument. A timer circuit activates the motor for a period of time to cause the instrument to advance to at or near the end of the endoscope. Once the instrument stops, the operator can advance the instrument manually.

9 Claims, 9 Drawing Sheets

Section A-A

Section B-B

60 — Attach shuttle 11 onto endoscope 10

61 — Feed instrument 26 into shuttle 11

63 — Activate shuttle 11 to advance instrument 26 and start timer

65 — Instrument 26 advances through endoscope 10

67 — Timer circuit 25 automatically stops instrument 26

68 — Manually advance instrument 26 and perform procedure

69 — Retract instrument 26

MOTORIZED ENDOSCOPIC INSTRUMENT DRIVE MODULE

TECHNICAL FIELD

The present disclosure invention relates endoscopes, more particularly, to systems for advancing instruments through the working channel of endoscopes.

BACKGROUND

Long flexible endoscopes are used to conduct diagnostic examination and therapeutic procedures on body cavities including the esophagus, stomach, bile duct, pancreatic duct, small bowel, colon, ureter, kidney, and nasal sinuses, among others. For therapeutic interventions, multiple extended length flexible instruments are inserted through the working port in the handle on the proximal end of the endoscope. Endoscopic therapeutic interventions generally necessitate frequent insertions, removals, and exchanges of multiple extended length flexible instruments by the physician, and each instrument insertion and removal is cumbersome due to the length of the instrument, particularly if it is performed by a single individual. Endoscopic instruments include graspers, scissors, biopsy forceps, and snares containing movable elements on their distal ends and control actuators such as ringed forceps grips on their proximal end. Typically instrument insertion into the endoscope involves grasping the distal portion of the instrument by hand and advancing the instrument tip through the fluid tight elastic seal covering the instrument port, followed by serial advancement of a short length of the flexible instrument through the working channel of the endoscope until the distal tip of the instrument lies near the distal tip of the endoscope. Caution must be applied to avoid sudden instrument exit from the distal end of the endoscope, as uncontrolled instrument exit may easily cause injury to adjacent anatomic structures or bowel perforation.

An instrument shuttle device that contains a power cable that connects to an external power source can interfere with normal manipulation of the endoscope by the physician and add to the technical challenge of a difficult endoscopic procedure. Furthermore, an attachment that significantly alters the weight balance or the profile of the endoscope handle would alter physician control of the endoscope with potential negative clinical effects on the patient.

Previous endoscope instrument advancement devices exhibit a large profile, either composed of multiple units, or attaching to the working handle of the endoscope via an additional mounting plate structure. Attachments that add bulk and weight to the working handle of an endoscope make manipulation of the endoscope controls cumbersome for the physician performing the procedure and therefore may increase the risk of complications such as blood vessel injury or intestinal perforation during the procedure. Endoscope manipulations routinely performed during an endoscopic procedure include rotation of the endoscope, articulation of the tip of the endoscope, and application of flexible instruments in the operating channel of the endoscope. Endoscopic instrument advancement devices that are reusable and require cleaning and sterilization before use add an additional hurdle to its application in an endoscopic procedure. An endoscopic instrument shuttle device is desired that expediently advances a lengthy endoscopic instrument through the working channel of a flexible endoscope and reduces uncontrolled instrument exit.

SUMMARY

Embodiments disclosed herein provide a cordless, sterile, single-use instrument shuttle device for the physician that does not require cleaning, disinfection, and re-sterilization by the medical facility, processes that add significantly to the manpower and workload requirements for each endoscopic procedure. For example, the device may be a compact, self-contained, cordless, battery powered unit that attaches to the standard instrument insertion port on the handle of a flexible endoscope. The device may include at least one electric motor that rotates a pair of drive wheels to advance and retract flexible endoscopic instruments through the working channel of the endoscope. Such embodiment includes a timer circuit configured to, upon an input signal, cause the wheels to rotate for a time period required to move the instrument toward the distal end of the endoscope. The device includes at least one battery to power the timer circuit and the motor(s) and an attachment port for coupling the shuttle to an endoscope.

In some embodiments, the drive wheels may be made of ethylene vinyl acetate (EVA) and may be placed in contact or in compressive contact with each other. Likewise, the wheels may be placed in compression in the anterior-posterior axis (side faces) by means of contact with a rigid housing that constrains the drive wheels. Constant compression between the contacting surfaces of the drive wheels ensures that the flexible endoscopic instrument will be advanced and retracted without slippage, in case the surface of the instrument is wet or moist. Compression of the drive wheels by an enclosed frame or outer housing ensures that the instrument does not slip out of position between the drive wheels during advancement and retraction. An inlet funnel tube that may contain a proximal gas tight O-ring seal allows insertion of the instrument into the contacting surfaces of the drive wheels, and an outlet funnel tube guides the instrument into the working port of the endoscope, for example via a connector that rigidly attaches the drive module to the working port. The inlet funnel and the outlet funnel may taper in shape to help locate and guide the instrument. The proximal seal maintains gas distention in the event that gas insufflation is used during the endoscopic procedure; and by providing slight resistance against the instrument, it assists with initial instrument insertion into the endoscopic instrument shuttle device. The outlet connector may rigidly attach to the working port of the endoscope via multiple setscrews that clamp onto the inlet ring on the working port.

During endoscopic instrument insertion, it is important that the instrument tip halts its advancement short of exiting out of the distal tip of the endoscope to avoid unintended injury to anatomic structures such as the bowel wall. A limit on instrument advancement may be performed using an integrated circuit timer (e.g., a 555 timer) switch that is activated upon depression of the instrument advancement switch, which cuts off power to the motors in the advancement mode after a specified period of several seconds. A second untimed circuit may govern instrument retraction, or the timed circuit may be reversed to retract the instrument for the same duration as it is deployed.

In some embodiments, the wheels may have a density within a range of about 50-100 $kg/m^3$.

In some embodiments, the wheels may be made of a thermoplastic elastomer, a rubber, or an elastomer. In some embodiments, the wheels may be made of a foam material.

In some embodiments, the instrument shuttle includes an outer housing containing the drive wheels, at least one motor, a gearbox through which the motor drives the wheels, a timer circuit, and least one battery. The housing may constrain the side surfaces of the wheels enough to prevent axial deformation while allowing them to rotate to advance the instrument. The contact may cause an interference fit with the wheels in some embodiments to prevent the wheels from deforming out of plane.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention. For example, dimensions of some components may be exaggerated relative to other components. Further, it is to be understood that other embodiments may be utilized, and structural and/or other changes may be made without departing from claimed subject matter. It should also be noted that directions and/or references, for example, proximal, distal, up, down, top, bottom, and so on, may be used to facilitate discussion of drawings and/or are not intended to restrict application of claimed subject matter. Therefore, the following detailed description is not to be taken to limit claimed subject matter and/or equivalents.

DETAILED DESCRIPTION

Embodiments of the present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. Furthermore, while several embodiments are described, the scope of embodiments should not be construed to be limited to those set forth herein.

As used herein, and unless the context indicates otherwise, the term "button" or "switch" may be used to describe any type of hand control mechanism such as a button, switch, or knob or any other manual control interface that provides a control input resulting in a binary on/off switch, a proportional control interface, or a momentary switch/button.

Figure 1:
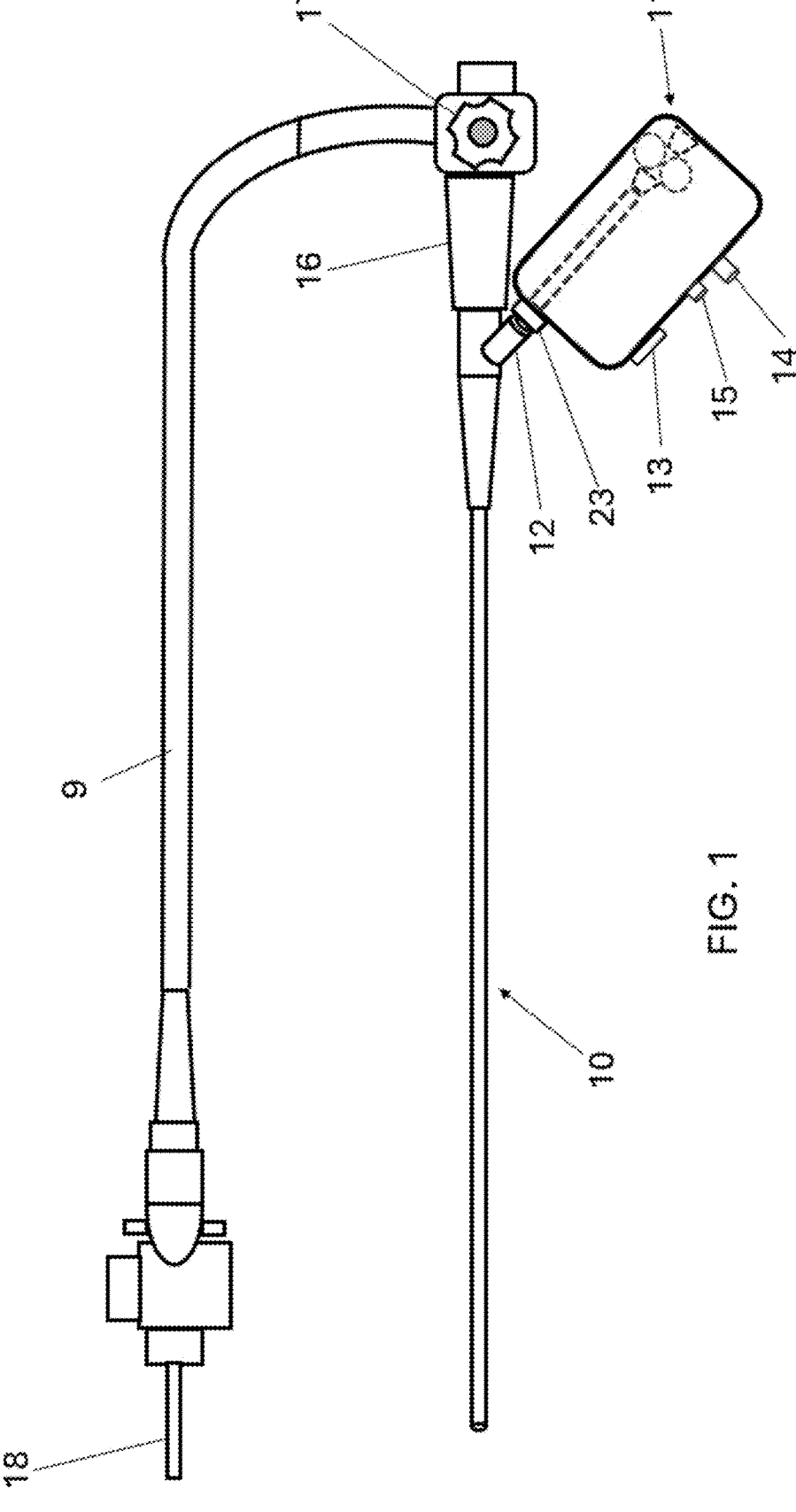
FIG. 1 shows the orientation of an exemplary endoscopic instrument shuttle device connected to the instrument insertion port of a flexible endoscope.

FIG. 1 shows an embodiment of the instrument shuttle module 11 connected to a flexible endoscope 10. The self-contained instrument shuttle module 11 attaches to the instrument port 12 of the flexible endoscope 10 via shuttle connector 23. The instrument port 12 comes off at an angle to the endoscope handle 16. The endoscope handle 16 also contains control knob 17 that angulates the tip of the endoscope 10. The proximal portion of the cable 9 connected to the endoscope 10 contains a fitting 18 that inserts into a light source to illuminate the examination field. The instrument shuttle module 11 has a small profile that angles away from the endoscope handle 16, to avoid compromising the manipulation and actuation of control knob 17. The instrument shuttle module 11 may contain a power switch 13, an instrument advancement control button 14, and an instrument retraction control button 15 on its side for ergonomic access and actuation.

Figure 2A:
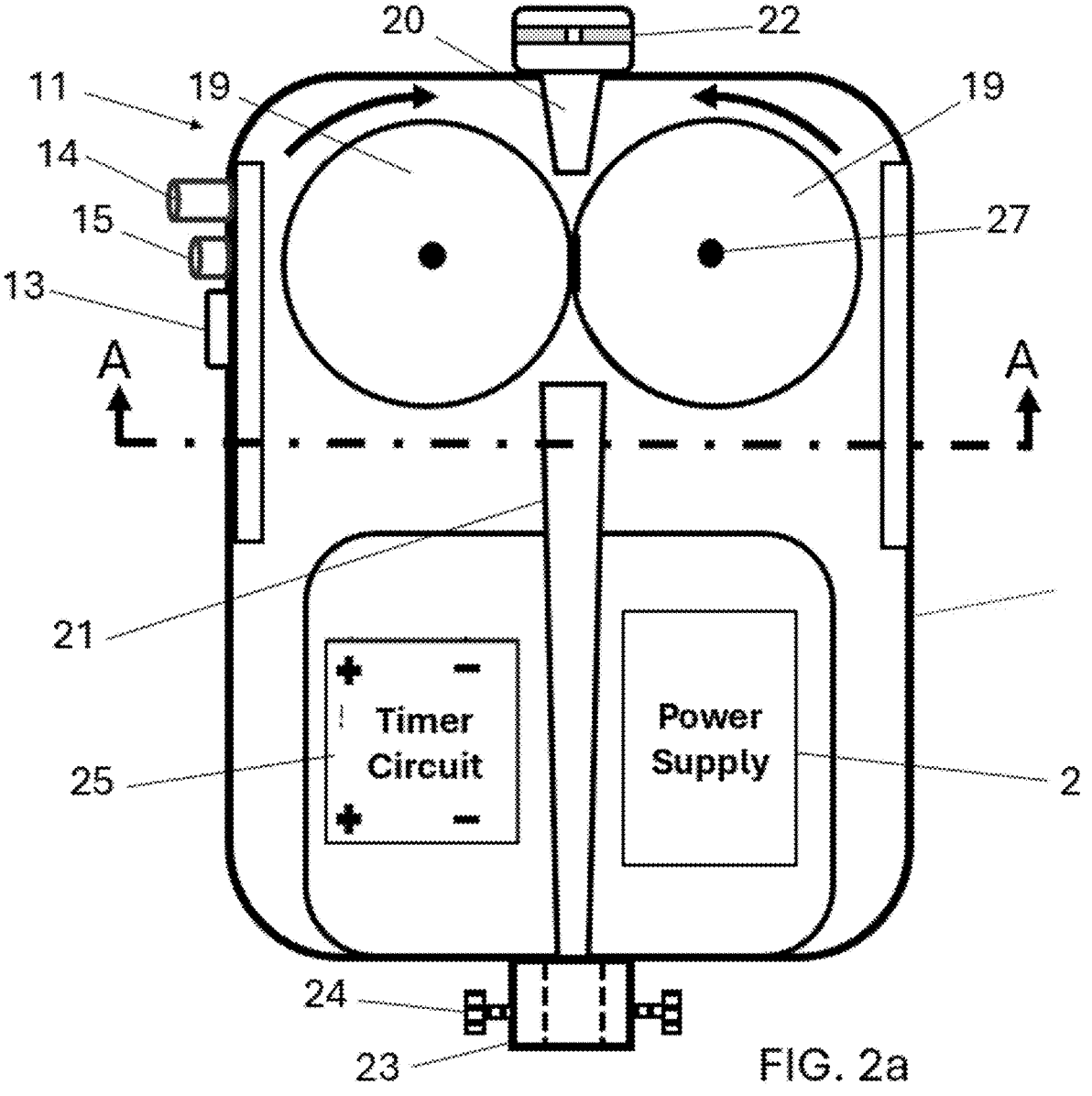
FIGS. 2a and 2b illustrate the functional components contained in embodiments of the endoscopic instrument shuttle devices disclosed herein.

FIG. 2a shows the components contained in the instrument shuttle module 11 according to an embodiment. Two wheels 19 are each rotated by or about an inner shaft 27. The wheels 19 are compliant such that they deform to grip the instrument as it feeds between the wheels. Candidate wheel materials include but are not limited to polymers, such as high-density ethylene vinyl acetate foam, elastomers, rubbers, and thermoplastic elastomers. In some embodiments, an input funnel 20 accepts an endoscopic instrument and guides the instrument towards the mating surfaces of the drive wheels 19. A fluid tight seal 22 resides proximal to the input funnel 20. The input funnel 20 guides the instrument into the wheels, as such, it may have a tapered profile as shown, or it may be swaged so as to accept and guide the instrument. As used herein, "swaged" is considered to be "tapered" or a form of taper for purposes of this disclosure. An output funnel 21 accepts and guides the endoscopic instrument as it is driven distally past the wheels. The output funnel 21 may have a tapered profile as shown, or it may be wider (e.g. swaged or chamfered) at the proximal end to capture the instrument with the remainder of the funnel being a straight tube. The output funnel 21 directs the instrument out of the shuttle module 11 via a shuttle connector 23, which attaches to the instrument port of the endoscope by, for example, multiple setscrews 24 or any other means for attaching and removing the shuttle module 11 quickly and easily. The instrument shuttle module 11 also houses a timer circuit 25, and a power supply 26 (e.g., one or more batteries) that powers the module. The timer circuit 25 may be any digital or analog circuit configured to switch an output after a set period of time. For example, the timer circuit 25 may be a 555 timer, a microcontroller, or any other integrated circuit or circuit board capable of performing a timing function.

The instrument shuttle module 11 is completely self-contained, and no extraneous power cables wires, or connecting frameworks exist that may impede physician manipulation of the flexible endoscope or its control knob. The shuttle module 11 may be supplied as a low-cost, sterilized, single-use disposable that can be attached to a standard endoscope easily so that the operator can quickly advance an instrument to the proper position safely through the endoscope. The module may be sterilized by any suitable sterilization method for medical devices such as gamma radiation, ethylene oxide gas, or electron beam sterilization.

Figure 2B:
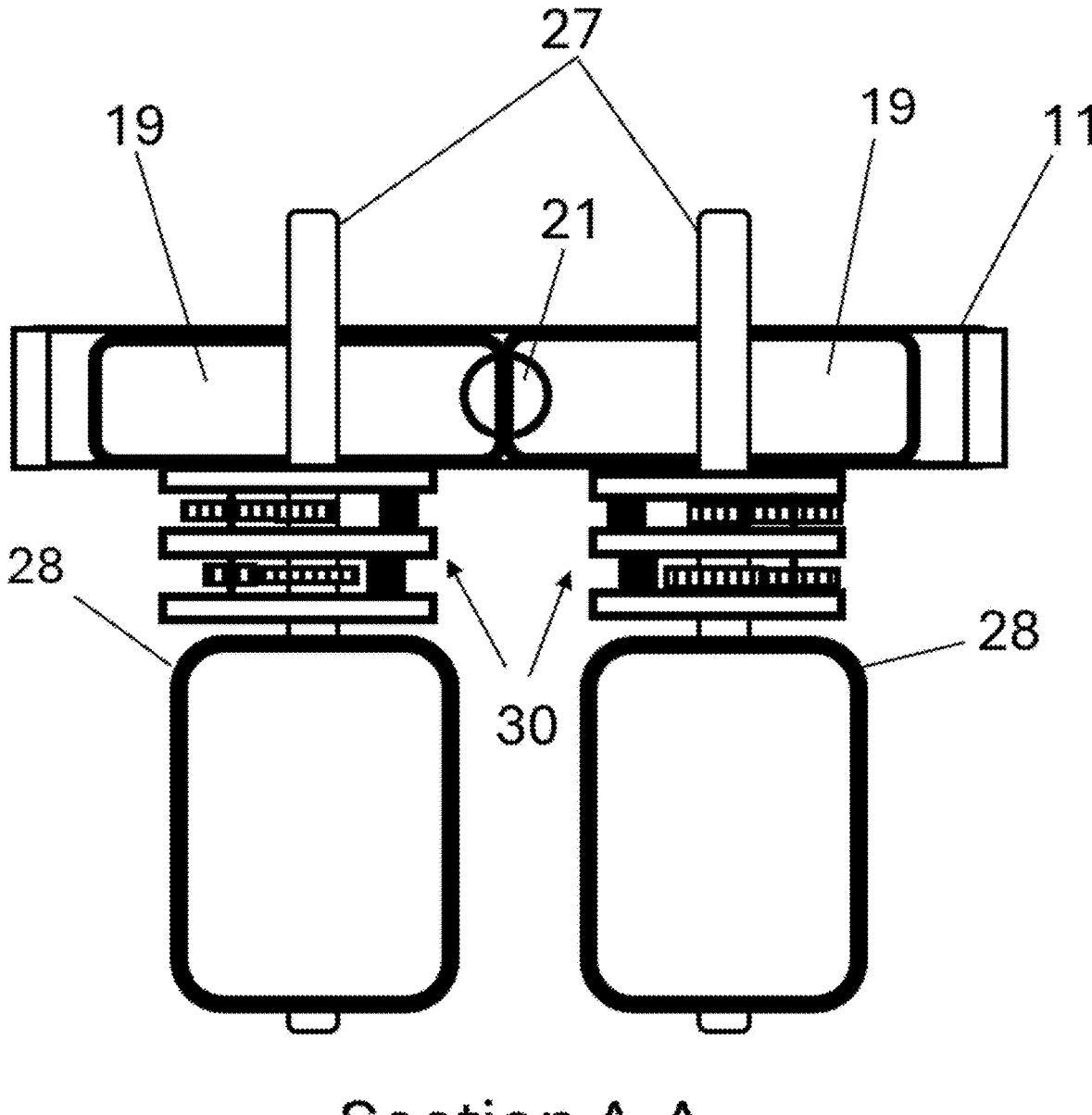

In some embodiments, the endoscopic instrument shuttle module 11 has three control switches. A main power switch 13 prevents drainage of the power supply 26 (e.g., batteries) to extend the shelf life of the module 11. The instrument advancement control button 14 and the instrument retraction control button 15 may be spring-loaded push button switches, such as momentary switches or any other hand activated switch. The timer circuit 25 is connected only to the instrument advancement control button 14 and activated when the instrument advancement control button 14 is depressed and power is provided to the motor to turn the drive wheels 19. The timer circuit 25 cuts off power to the motor after a predetermined period of several seconds, limiting instrument advancement to prevent the tip of the flexible endoscope from moving beyond a desired distance relative to the end of the endoscope. FIG. 2b is a sectional view (A-A) of the endoscopic instrument shuttle module 11 illustrating rotation of two drive wheels 19 by two electric motors 28 with attached gearboxes 30. Shafts 27 rotate the drive wheels 19 in opposite directions. In some embodiments, the module 11 may contain only one motor that drives both wheels through a gearbox. In other embodiments, there may be one motor per wheel, and they may be driven directly without a gearbox or via gearboxes, and gearboxes may be separate or, in some embodiments, integrated with the motors. The instrument shuttle module 11 is self-contained in that it has no external connections, other than to an endoscope 10, as shown in FIG. 1, and the drive components (e.g., and electronics) are contained within the shuttle module 11. In embodiments where the instrument shuttle module is a single-use disposable medical device, low-cost and minimization of components and integration of components may be key design objectives.

Figure 3A:
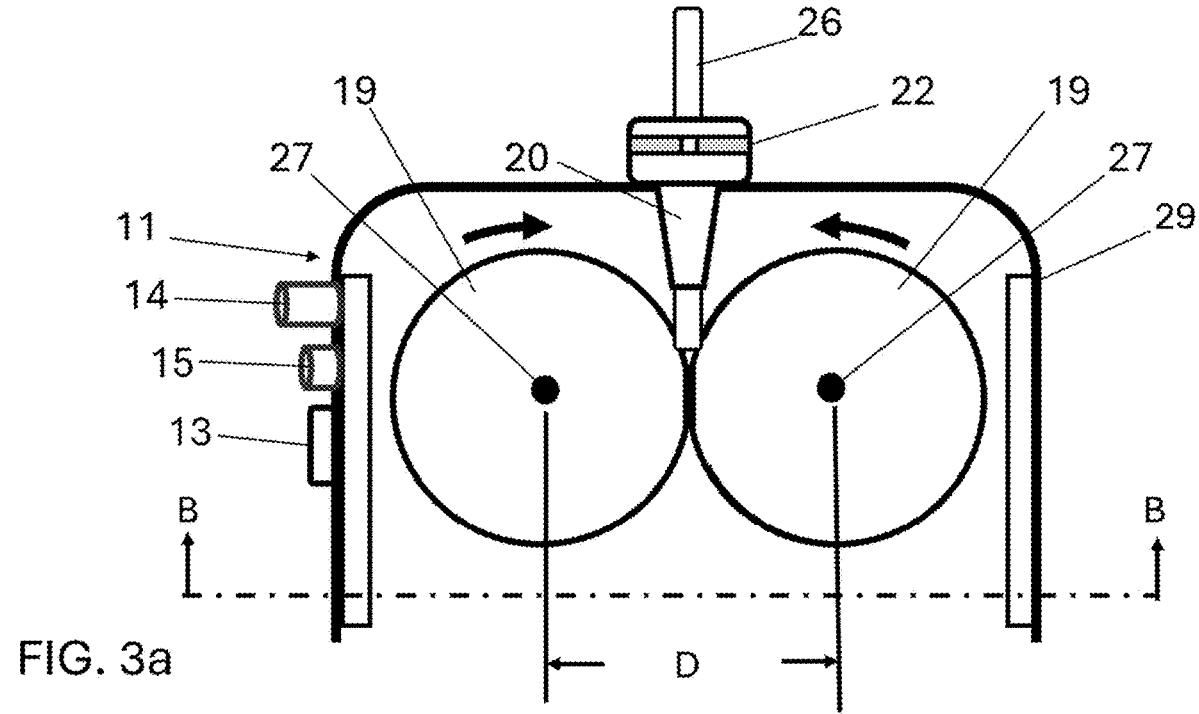
FIG. 3a shows the drive mechanism portion of an embodiment of an instrument shuttle, illustrating formation of two axes of compression on the drive wheels to maintain proper advancement and retraction of the endoscopic instrument.

FIG. 3a depicts a portion of the instrument shuttle module 11 showing the configuration of the drive wheels 19 in the instrument shuttle module 11. In some embodiments drive wheels 19 are constructed of high-density ethylene vinyl acetate (EVA) foam, with a density of approximately 85 kg/m$^3$ or for example a density within a range of about 50-100 kg/m$^3$. The flexible foam material allows the wheels to deform and grip the instrument as they advance and retract the instrument. In some embodiments, the two drive wheels 19 are constrained in constant compression with each other, for example, as each drive wheel 19 has an outer diameter of about 30 mm, and their central axes are separated by about an inch, or about 25 mm (distance "D" in FIG. 3a), resulting in approximately 2.5 mm of radial compression per wheel before an instrument is introduced. The compliant materials of the drive wheel 19 and their compressed state ensure that instrument advancement occurs precisely without slippage, even with damp or wet endoscopic instruments. In some embodiments, the wheels have a gap between their outer radial surfaces such that the gap is smaller than the diameter of the instrument that is introduced between them.

The technique for instrument advancement involves inserting the tip of the endoscopic instrument 26 through the fluid tight seal 22 and the input funnel 20 and wedging the endoscopic instrument 26 into the compressed drive wheels 19; introduction is tactilely indicated by the increased resistance observed by the operator upon axial instrument advancement. Next, the advancement control button 14 is depressed and held down to advance the endoscopic instrument 26 through the flexible endoscope driven by the counter rotating drive wheels 19. The timer circuit 25 automatically stops advancement of endoscopic instrument 26 short of the distal end of the endoscope based on the feed rate and the length to the distal end of the endoscope. At this point, the advancement control button 14 no longer triggers movement of the drive wheels 19. Once the instrument 26 reaches the distal end of the endoscope and the timer stops advancement, the surgeon manually advances the endoscopic instrument 26 out of the endoscope under visual guidance, avoiding any potential bowel or organ damage that may occur due to uncontrolled instrument advancement. For instrument retraction, the instrument retraction control button 15 is depressed and held down until the endoscopic instrument 26 exits the flexible endoscope. In some embodiments, the buttons 14 and/or 15 may switch the timer on such that the timer stays on after the button is released, allowing the timer to maintain the motor running for the set duration without requiring the operator to hold the button down.

In some embodiments, the shuttle module may have a selector switch for selecting different lengths of endoscope (i.e., different timer settings), while in other embodiments, the shuttle module may be specific to one length and/or brand/model of endoscope, so that it has a fixed timer setting. Furthermore, in some embodiments, the shuttle may have a sensor that detects entrance of an instrument into the shuttle and automatically starts the timer and the wheels to advance the instrument distally for a set period of time. The sensor may be any suitable sensor for detecting presence of an object, such as a contact sensor or an optical sensor.

The compression forces from the drive wheels 19 must be large enough to create the required friction force to advance the instrument 26 even when the instrument and/or wheels are wet. As the instrument 26 is grasped by the wheels, it may tend to spring out of place, that is, out of the plane of the wheels due to the compliance of the wheels and/or axial play of the wheels 19. This can cause the instrument 26 to hang up or bind or to miss being captured by the output funnel 21 as it translates distally through the instrument shuttle module 11. Therefore, in some embodiments, the drive wheels may be constrained in the axial direction (i.e., referring to the axis represented by the shaft 27 about which the wheels rotate, herein referred to as the "axial" direction). As used herein, the side surfaces of the wheels refer to the sides of the wheels, that is, the surface orthogonal to the axis of the wheels, in contrast to the radial surface of the wheels that grip and drive the instrument. In some embodiments, the drive wheels 26 may have a rigid hub that stiffens the wheel to reduce out of plane flexing, that is, flexing in the axial direction.

Figure 3B:
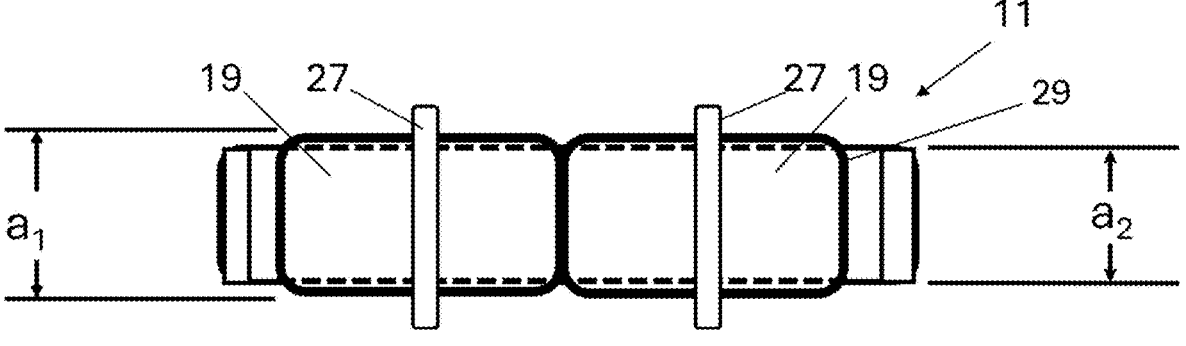
FIG. 3b shows an end view inside of an embodiment of an instrument shuttle device where the wheels are constrained by the housing of the device.
Figure 3C:
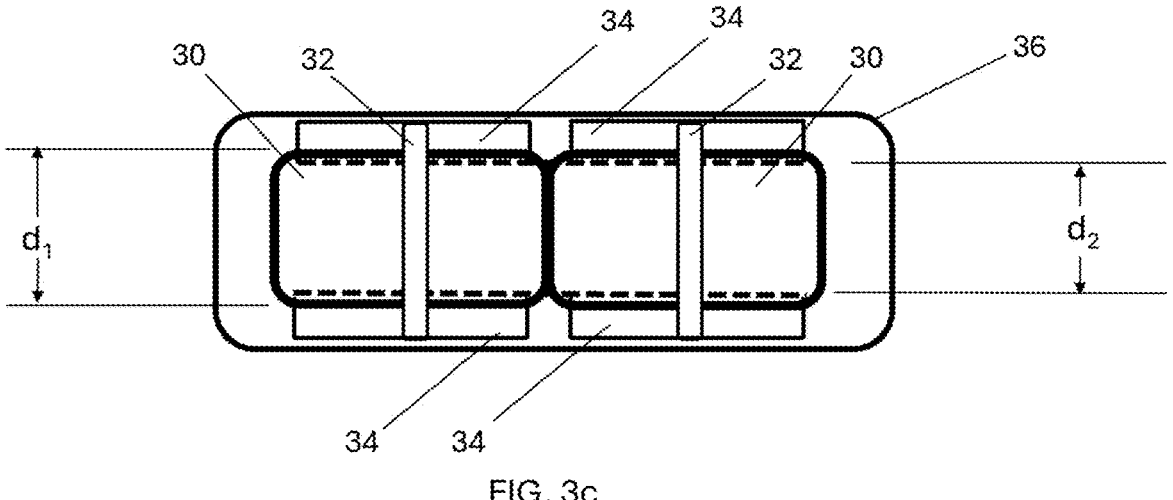
FIG. 3c shows an end view inside an embodiment of an instrument shuttle device where the wheels are constrained by an intermediate structure in the device.

As the instrument shuttle module 11 may be a single-use disposable device, minimization of part count and complexity may be desired to reduce cost. FIG. 3b illustrates an embodiment wherein the drive wheels 19 may be placed in compression on their side surfaces, that is the surfaces orthogonal to the drive axis, by contact on their side surfaces with the housing 29 of the instrument shuttle module 11, in order to restrict or prevent axial flexing or axial movement of the wheels 19. As an illustrative example, if the resting thickness of the foam drive wheels 19 is 5.0 mm (a$_1$ in FIG. 3b), but the inside dimensional width of housing 29 is 4.78 mm (a$_2$ in FIG. 3b), this places the drive wheels 19 under continuous compression (i.e., an interference fit) between the front and back of the housing 29 of the instrument shuttle module 11. FIG. 3b shows the width of the drive wheels 26 in the relaxed state (e.g., at 5 mm thick) before being compressed within the housing 29 (dashed line) of the instrument shuttle module 11. Compression in this axis prevents slippage of endoscopic instrument 26 out of position between the two drive wheels 19 during advancement and retraction. Note that there may be other structural features within the shuttle module 11 instead of the housing 29 that contact and constrain the wheels from distorting axially. For example, FIG. 3c shows another embodiment in a similar view as FIG. 3b. In this example, intermediate structures 34 mounted inside the housing 36 contact the wheels 30 to constrain them from axial deformation. For illustration, FIG. 3c shows the width of the drive wheels $d_1$ in the relaxed state before being compressed by the intermediate structures 34 (having a distance therebetween of $d_2$ which is less than $d_1$). In general, the constraint on the wheels should be enough to prevent significant axial distortion while still allowing the motor (e.g., and associated gears) to drive the wheels.

Figure 4A:
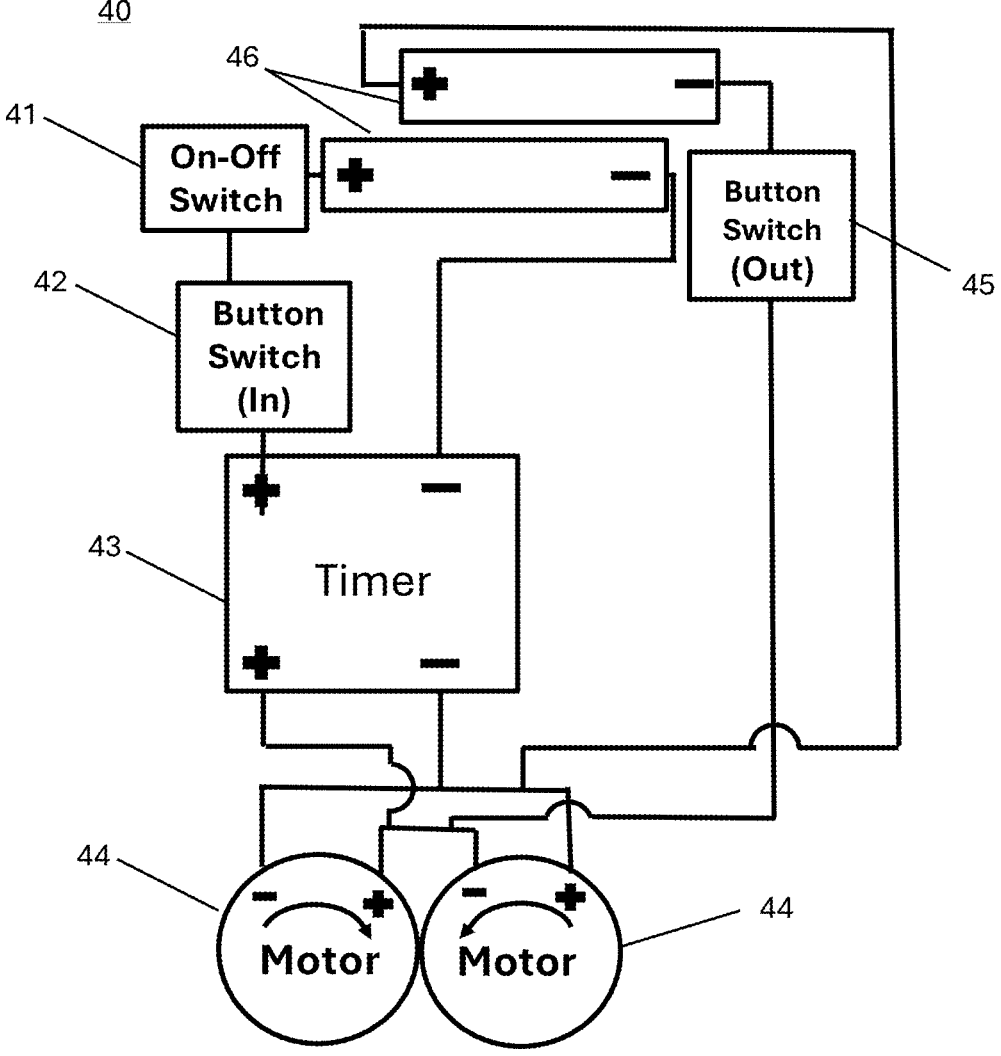
FIGS. 4a and 4b depict exemplary circuit diagrams for instrument shuttles with two different types of control switches.
Figure 4B:
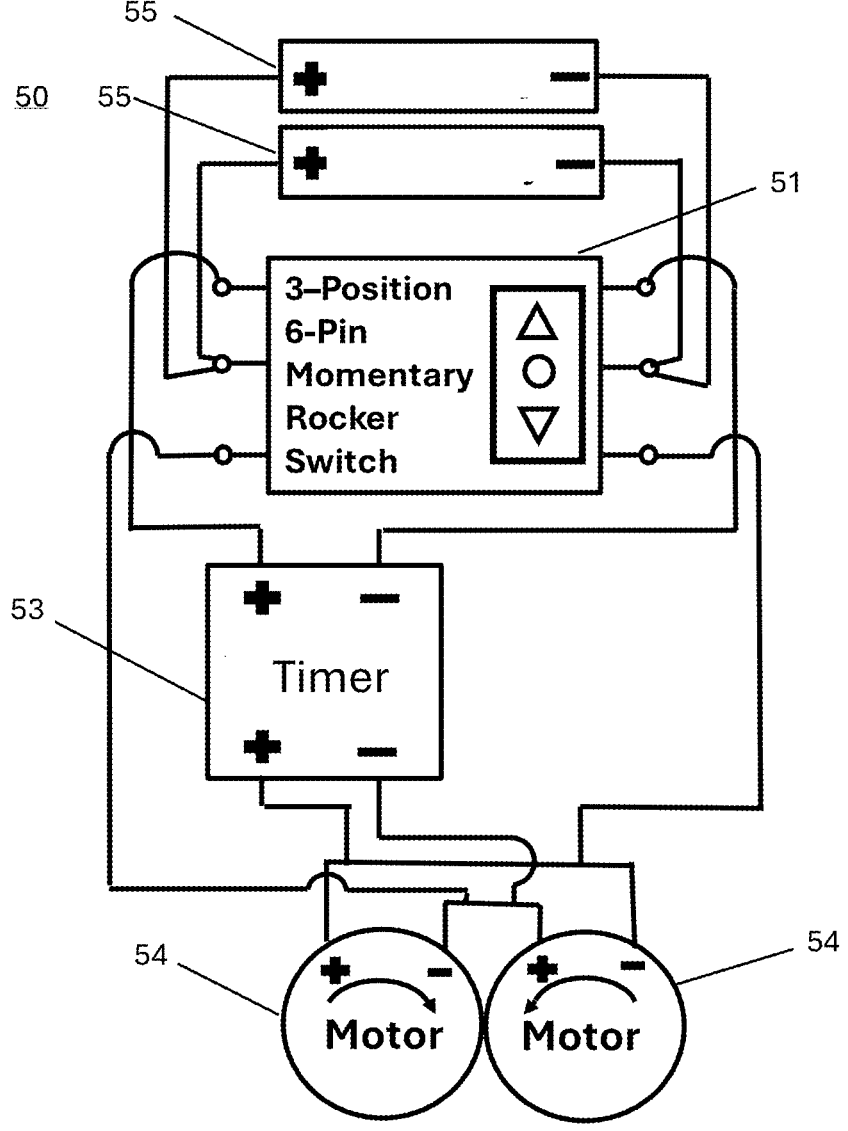

Now with reference to FIG. 4a which shows an embodiment of a simplified circuit 40 for an instrument shuttle device containing separate control buttons for instrument advancement and instrument retraction. The circuit 40 has an onboard power source comprising one or more batteries 46, an on/off switch 41, an "in" button switch 42 for driving the instrument into the endoscope, an "out" button switch 45 for retracting the instrument, and a timer circuit 43 for stopping the motors 44 and the instrument. FIG. 4b shows another embodiment of a circuit 50 for an instrument shuttle device having an onboard power source comprising one or more batteries 55, a 3-position momentary rocker switch 51 to control instrument advancement and instrument retraction functions, with the switch normally residing in an off position, and a timer circuit 53 for stopping the motors 54 and the instrument.

In the embodiments of FIGS. 4a and 4b, the timer circuit 43 (and 53) may be any digital or analog circuit configured to switch an output off after a set period of time. For example, the timer circuit may be a 555 timer, a microcontroller, or any other integrated circuit or circuit board capable of performing a timing function. In some embodiments, the timer circuit 43 (and 53) may count time cumulatively. For example, if the "in" button switch is momentarily switched on and then off, the timer counts the on time and adds it to any other on/off cycles to arrive at the time at which the instrument is expected to reach the end of the endoscope, at which time the timer switches the motors off. "Batteries" referred to in the embodiments disclosed herein may be a single battery or multiple batteries such as standard 9V batteries, AA batteries, or AAA batteries, for example.

Figure 5:
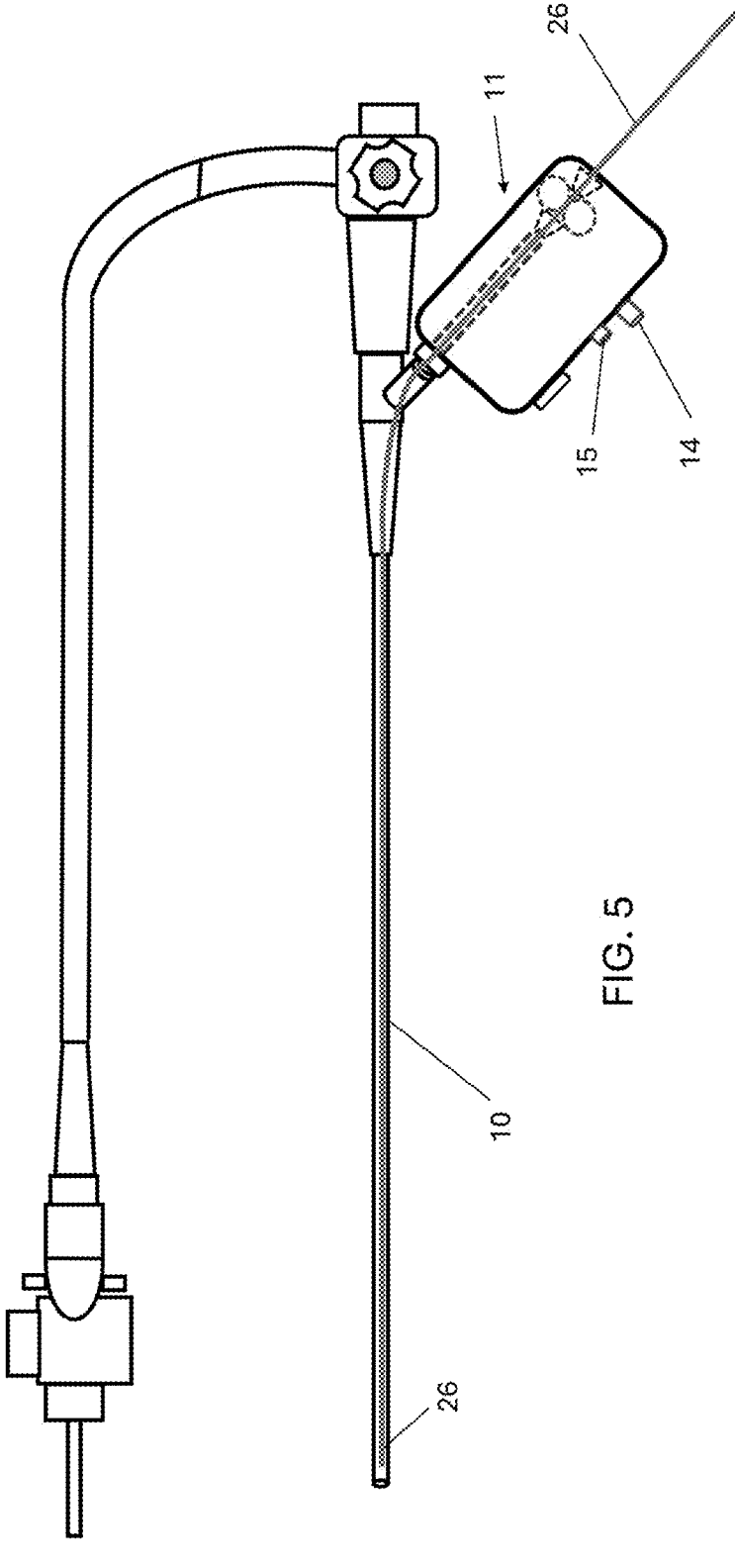
FIG. 5 illustrates instrument advancement, with the tip of the endoscopic instrument automatically stopping short of exiting the working channel of an endoscope.

FIG. 5 illustrates the position of the tip of the endoscopic instrument 26 short of the distal end of flexible endoscope 10 upon depression of the instrument advancement control button 14. Full advancement of the endoscopic instrument 26 out of the distal end of flexible endoscope 10 is performed manually under direct endoscopic visual guidance. That is, the operator pushes the instrument 26 forward through the shuttle module 11 which, in some embodiments, overrides the wheels and associated motor/gears so that the instrument 26 can be positioned at a desired location beyond the tip of the endoscope 10. After use, the operator can actuate the retraction control button 15 until the instrument 26 withdraws from the endoscope 10 by a desired amount.

Figure 6:
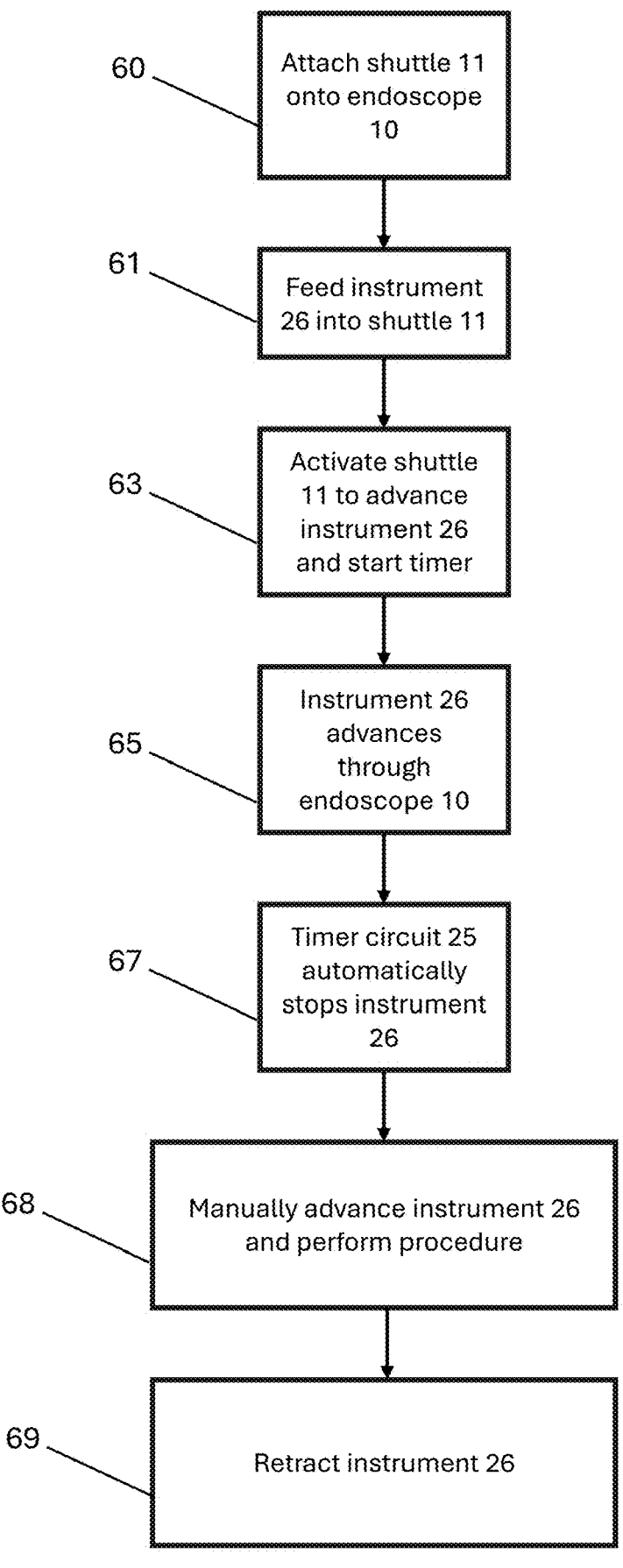
FIG. 6 is a flowchart illustrating a method of use according to embodiments disclosed herein.

Now with reference to FIG. 6 which illustrates an embodiment of a method for implementing an instrument shuttle according to the present disclosure. At step 60 the shuttle module 11 is attached to the endoscope 10, for example by set screws or some other easily attachable/removable mechanism. At step 61, the instrument 26 is fed into the shuttle 11 and once in the shuttle 11, the shuttle 11 can be activated as in step 63 to trigger the timer circuit 25 either automatically via a sensor detecting the instrument 26 or manually by the operator pressing a button. At step 65, the instrument advances through the endoscope 10 and then is automatically stopped at step 67 when the timer circuit 25 times out and stops the motor(s) in the shuttle 11. Next, the operator manually advances the instrument 26 and performs the procedure on the patient. The instrument 26 is advanced by manually pushing it through the shuttle 11 and the endoscope 10 where it overrides the wheels so that they rotate. In some embodiments, the wheels may have a significant amount of resistance to manual rotation due to friction and/or a gear box. In this case, the wheels or gearbox may have a clutch that releases at a particular override force allowing them to rotate manually.

Finally, as illustrated in step 69, the operator retracts the instrument 26 from the body and from the shuttle 11. This may be done by manually pulling the instrument out or by activating the shuttle 11 to retract the instrument 26, or a combination thereof; for example the operator may pull the instrument 26 out of the body such that the end enters the endoscope 10, then use the shuttle 11 to retract the instrument 26 the remainder of the way out of the endoscope 10. Such retraction may be automated by the timer, or it may be manually controlled, i.e., by the operator pressing the button causing the instrument 26 to move distally.

While this invention(s) has been particularly shown and described with references to example embodiments thereof, it will be understood by those skilled in the art that various changes in form and details may be made therein without departing from the scope of the invention(s) encompassed by the appended claims. While the above is a complete description of the certain embodiments of the invention, various alternatives, modifications, and equivalents may be used. The various devices and method steps of the embodiments disclosed herein may be combined or substituted with one another, or performed in a different order, and such alternative embodiments fall within the scope of the claimed invention(s). Therefore, the above description should not be taken as limiting in scope of the invention (a) which is defined by the appended claims.

Embodiments disclosed herein have been described in the context of an endoscope, however, the inventions may be applied to other anatomical access devices where an instrument is advanced and must be stopped at a desired distance.

What is claimed is:

1. A cordless endoscope instrument shuttle module for advancing an instrument into an endoscope, the shuttle module comprising:
   a housing containing:
      a pair of drive wheels configured to grip and propel an instrument between the wheels;
      at least one motor configured rotate the wheels in a direction to propel the instrument distally into the endoscope and in an opposite direction to extract the instrument from the endoscope;
      a timer circuit configured to, upon an input signal, cause the wheels to rotate for a time period suitable to move the instrument to near the distal end of the endoscope;
      at least one battery to power the timer circuit and the at least one motor; and
      wherein each wheel is constrained by an interference fit with the housing to restrict axial deformation.

2. The shuttle module of claim 1 further comprising an output funnel distal to the wheels to guide the instrument towards the exit of the module.

3. The shuttle module of claim 2 wherein the output funnel tapers in the distal direction.

4. The shuttle module of claim 1 further comprising an input funnel proximal to the wheels to guide the instrument towards the wheels.

5. The shuttle module of claim 1 wherein the timer is a 555 timer.

6. The shuttle module of claim 1 wherein the wheels are made of ethylene vinyl acetate (EVA).

7. The shuttle module of claim 6 wherein the EVA has a density within a range of about 75-100 kg/m$^3$.

8. The shuttle module of claim 1 wherein the wheels are made of one of a group consisting of a thermoplastic elastomer, a rubber, and an elastomer.

9. The shuttle module of claim 1 wherein the wheels are made of a foam material.

* * * * *